(12) United States Patent
Portugal

(10) Patent No.: US 6,727,061 B2
(45) Date of Patent: Apr. 27, 2004

(54) METHODS FOR IDENTIFYING SPECIES OR SHIGELLA AND E. COLI USING OPERON SEQUENCE ANALYSIS

(75) Inventor: Frank H. Portugal, Potomac, MD (US)

(73) Assignee: Cabtec, Inc., Potomac, MD (US)

( * ) Notice: Subject to any disclaimer, the term of this patent is extended or adjusted under 35 U.S.C. 154(b) by 0 days.

(21) Appl. No.: 09/027,089

(22) Filed: Feb. 2, 1998

(65) Prior Publication Data

US 2003/0087227 A1 May 8, 2003

Related U.S. Application Data

(60) Provisional application No. 60/038,117, filed on Feb. 20, 1997.

(51) Int. Cl.[7] .......................... C12Q 1/68; C12P 19/34; C07H 21/04
(52) U.S. Cl. ..................... 435/6; 435/91.1; 536/23.1; 536/24.3; 536/24.32
(58) Field of Search .................... 435/6, 91.1, 91.2; 536/23.1, 24.3, 24.32, 24.33

(56) References Cited

U.S. PATENT DOCUMENTS 5,374,718 A * 12/1994 Hammond ............... 536/24.32
5,601,984 A *  2/1997 Kohne .......................... 435/6
5,714,321 A *  2/1998 Hogan .......................... 435/6

OTHER PUBLICATIONS

Cilia et al. (Mol. Biol. Evol. vol. 13, pp 451–461), Feb. 26, 1996.*
Anderson, Gene Probes 2: hybridization strategies. Oxford University Press, New York, pp 1–29 Feb. 1996.*
Accession No. X80728, Mar. 1996.*
Accession No. U68651, Jul. 1997.*
Dyson, N. J. Essential Molecular Biology vol. II A practical approach. Brown., T.A. ed. Oxford University Press, Oxford, 1992.*
N. Harris and D.G. Wilkinson, "In Situ Hybridization: Application to Developmental Biology and Medicine" 1990.
R. Rapley, "The Nucleic Acid Protocols Handbook," Humana Press, 2000.
B.D. Hames and S.J. Higgins, "Nucleic Acid Hybridization A Practical Approach," IRL Press, 1985.
J.J. Greene and V.B. Rao, "Recombinant DNA Principles and Methodologies," Marcel Dekker, 1998.
J.M. Polak and J. O'D. McGee, In Situ Hybridization: Principles and Practice, Second Edition, Oxford, 1998.
T. Schwarzacher and P. Heslop–Harrison, "Practical In Situ Hybridization," Springer, 1999.
D.G. Wilkinson, "In Situ Hybridization," Oxford University Press, 1998.
G.R. Coulton and J. de Belleroche, In Situ Hybridization Medical Applications, Kluwer Academic Publishers, 1992 p. 24, 31.
D.H. Persing et al., "Diagnostic Molecular Micro–biology," American Society for Microbiology, 1993 pp. 94–95,
E. Stackebrandt and M. Goodfellow, "Nucleic Acid Techniques in Bacterial Systematics," John Wiley, 1991 pp. 207–216; 29–31.
J.E. Beesley, "Immunohistochemistry and In Situ Hybrid–ization in the Biomedical Sciences," Birkhauser, 2001 pp. 122–123.

* cited by examiner

Primary Examiner—Jehanne Souaya Sitton
(74) Attorney, Agent, or Firm—Millen, White, Zelano & Branigan, P.C.

(57) ABSTRACT

A method for comparing the variable reactivity of multiple, differentially mutated copies of 16S subsequences found in a number of ribosomal RNA operons of a single bacterial cell is described. The application of this method for distinguishing between closely related organisms, such as the genera Escherichia and Shigella, and between species of Shigella including *S. boydii*, *S. dysenteriae*, *S. flexneri*, and *S. sonnei* using nucleic acid probes is also presented.

30 Claims, 2 Drawing Sheets

SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      oligonucleotide probe

<400> SEQUENCE: 1
cagcttgctc ttcgctgacg                                            20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      oligonucleotide probe

<400> SEQUENCE: 2
aaagcagctt gctctttgct                                            20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      oligonucleotide probe

<400> SEQUENCE: 3
cgacgcaacg cgaagaactt                                            20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      oligonucleotide probe

<400> SEQUENCE: 4
gaagcttgct tctttgctga c                                          21

<210> SEQ ID NO 5
<211> LENGTH: 30
<212> TYPE: DNA
<213> ORGANISM: Escherichia coli
<220> FEATURE:
<221> NAME/KEY: misc_feature
<222> LOCATION: (1)..(30)
<223> OTHER INFORMATION: Ribosomal RNA Operon

<400> SEQUENCE: 5
aacaggaaga agcttgctct tgctgacga                                  30

<210> SEQ ID NO 6
<211> LENGTH: 31
<212> TYPE: DNA
<213> ORGANISM: Escherichia coli
<220> FEATURE:
<221> NAME/KEY: misc_feature
<222> LOCATION: (1)..(31)
<223> OTHER INFORMATION: Ribosomal RNA Operon -continued

<400> SEQUENCE: 6
aacaggaaac agcttgctgt ttcgctgacg a                              31

<210> SEQ ID NO 7
<211> LENGTH: 31
<212> TYPE: DNA
<213> ORGANISM: Escherichia coli
<220> FEATURE:
<221> NAME/KEY: misc_feature
<222> LOCATION: (1)..(31)
<223> OTHER INFORMATION: Ribosomal RNA Operon

<400> SEQUENCE: 7
aacaggaaga agcttgcttc tttgctgacg a                              31

<210> SEQ ID NO 8
<211> LENGTH: 31
<212> TYPE: DNA
<213> ORGANISM: Escherichia coli
<220> FEATURE:
<221> NAME/KEY: misc_feature
<222> LOCATION: (1)..(31)
<223> OTHER INFORMATION: Ribosomal RNA Operon

<400> SEQUENCE: 8
aacaggaaac agcttgctct ttcgctgacg a                              31

<210> SEQ ID NO 9
<211> LENGTH: 31
<212> TYPE: DNA
<213> ORGANISM: Escherichia coli
<220> FEATURE:
<221> NAME/KEY: misc_feature
<222> LOCATION: (1)..(31)
<223> OTHER INFORMATION: Ribosomal RNA Operon

<400> SEQUENCE: 9
aacaggaaga agcttgcttc tttgctgacg a                              31

<210> SEQ ID NO 10
<211> LENGTH: 31
<212> TYPE: DNA
<213> ORGANISM: Escherichia coli
<220> FEATURE:
<221> NAME/KEY: misc_feature
<222> LOCATION: (1)..(31)
<223> OTHER INFORMATION: Ribosomal RNA Operon

<400> SEQUENCE: 10
aacaggaacg agcttgctgc tttgctgacg a                              31

<210> SEQ ID NO 11
<211> LENGTH: 31
<212> TYPE: DNA
<213> ORGANISM: Escherichia coli
<220> FEATURE:
<221> NAME/KEY: misc_feature
<222> LOCATION: (1)..(31)
<223> OTHER INFORMATION: Ribosomal RNA Operon

<400> SEQUENCE: 11
aacaggaagc agcttgctgc tttgctgacg a                              31

US 6,727,061 B2

METHODS FOR IDENTIFYING SPECIES OR SHIGELLA AND *E. COLI* USING OPERON SEQUENCE ANALYSIS

This application claims priority to U.S. provisional application Ser. No. 60/038,117, filed Feb. 20, 1997, which is incorporated by reference herein in its entirety.

FIELD OF THE INVENTION

This invention relates to a method for distinguishing among bacteria within the same taxonomic group based on the reactivity of specific 16S subsequences found within the ribosomal operons of the organisms, using probes during hybridization under conditions of increasing severity (stringency). Hybridization is the process whereby two strands of nucleic acid can interact and, if sufficiently matched in sequence, form a double-stranded structure. By the term probe is meant a marked, single-stranded nucleic acid sequence that is complementary to the nucleic acid sequences to be detected (target sequences). The use of this method of operon analysis for distinguishing the genera Escherichia from Shigella and for distinguishing among species of Shigella is demonstrated together with nucleic acid probes needed for conducting the analyses.

BACKGROUND OF THE INVENTION AND DESCRIPTION OF THE INVENTION

The terms *"Escherichia coli," "Shigella boydii," "Shigella dysenteriae," "Shigella flexneri,"* and *"Shigella sonnei"* refer to the bacteria classified as such in Bergey's Manual of Determinative Bacteriology, 8th Edition, R. D. Buchanan and N. E. Gibbons, Eds., William & Wilkins, 1974, pp. 290–339. Unless specified otherwise the term Shigella will refer collectively to the four species mentioned above.

Detection of Shigella is important for medical diagnosis, public health surveillance, food safety, and other applications. Cases of Shigella, which must be identified by species, are required to be reported to the Centers for Disease Control and Prevention, which tracks the incidence and prevalence of Shigella in every state in the United States and in the District of Columbia. Current methods of detection are neither simple, straightforward, nor absolute (J. J. Farmer, III and M. T. Kelly, Enterobacteriaceae, in A. Balows, Ed, Fifth Edition, Manual of Clinical Microbiology, Washington, D.C., American Society for Microbiology, 1991.)

Suspected colonies usually are grown on both MacConkey agar and xylose-lysine-deoxycholate agar. Colonies of Shigella missed on one medium may show up on the other. Many laboratories also use Hektoen enteric agar. Enrichment of less than optimum cultures may require GN broth. Selenite broth may be useful for isolating *S. sonnei*. Suspected colonies of Shigella require confirmation by culture on other types of growth media such as triple sugar iron or Kliger iron agar slants. Colonies that show an alkaline/acid reaction with no $H_2S$ or gas then must be screened further by serological analysis with antisera in order to identify each of the species of Shigella.

Even with these procedures, differentiating strains of Shigella from *Escherichia coli* has proved to be one of the most difficult problems for a clinical microbiology laboratory. Recommended guidelines are complicated by exceptions related to one or more Shigella species. The difficulties inherent in distinguishing these organisms often forces investigators to depend merely on the fact that two Shigella species (*S. boydii* and *S. flexneri*) are not as prevalent in the United States, although a significant number of cases do occur, as are the other two species in order to help solidify their diagnoses. Still, the guidelines conclude with the realization that no definitive rules on the identification of Shigella isolates can be made and complete biochemical and serological typing must be done in each instance.

It is yet another aspect of the invention to avoid the disadvantages associated with the traditional culturing and serological identification techniques and to employ nucleic acid probes to distinguish *Escherichia coli* from Shigella and to identify each of its four associated species.

Efforts to circumvent the difficult, expensive, and time-consuming procedures with a simple yet rapid molecular procedure for differentiating the genus Shigella from the genus Escherichia and for separately identifying each of the four individual species of Shigella has also proved difficult. This has been attributed, in particular, to the very close relatedness of *E. coli* and all four Shigella species by DNA-DNA hybridization (J. J. Farmer, III and M. T. Kelly, Enterobacteriaceae, in A. Balows, Ed, Fifth Edition, Manual of Clinical Microbiology, Washington, D.C., American Society for Microbiology, 1991.)

Kyriaki Parados and Janice McCarty (U.S. Pat. No. 5,648,481) have identified a set of nucleic acid probes for detection of the genus Shigella and/or *E. coli* (EIBC) based on specific chromosomal sequences and fragments of Shigella. These probes can neither distinguish between *E. coli* and Shigella nor can they separately distinguish between one species of Shigella and another. In addition, the relatively large probes (approximately 40 nucleotides each) require hybridization overnight followed by exposure for 15 hours to x-ray film to produce autoradiographs.

Alessio Fasano, Myron M. Levine, James P. Nataro, and Fernando Noriega (U.S. Pat. No. 5,589,380) targeted the enterotoxins of *Shigella flexneri*2a and produced antibodies to the same, which might be useful primarily for the identification of *S. flexneri*. Kyriaki Parodos, Hsien-Yeh Hsu, Daid Sobell, Janice M. McCarty, and David J. Lane (U.S. Pat. No. 5,084,565) devised probes capable of hybridizing to rRNA of both *E. coli* and Shigella species but unable to discriminate among them. Phillippe Sansonetti, Catherine Boileau and Hélène D'Hauteville (U.S. Pat. No. 4,992,364) targeted the 140 MDalton virulence plasmid of *S. flexneri*. Their probes are relatively large, ranging in size from about 11.5 kbases to 27 kbases, and identify only combined strains of Shigella and *E. coli* carrying the virulence plasmid. Long-term hybridization (overnight) is followed by 6 hours of exposure to produce autoradiographs.

A subsequence of ribosomal RNA (rRNA) or its gene presents a potential target for separate identification of *E. coli* and each of the four species of Shigella through hybridization with appropriate DNA or RNA probes. Portions of rRNA have been found not to be conserved among diverse bacterial species, making them potential hybridization targets for distinguishing between one taxonomic group and another. David E. Kohne (U.S. Pat. No. 5,601,984) discusses such a method for detecting and quantitating organisms. But Kohne does not provide the teaching necessary to make Shigella species-specific probes.

Furthermore, Kohne does not teach how to distinguish among very closely related organisms using probes where a subsequence of a rRNA subunit or rRNA subunit gene is not specific to the taxonomic group (qualitative difference) but rather occurs as multiple but slightly differentiated copies in different proportions among multiple operons for the RNA genes (quantitative difference). An operon is defined as a group of contiguous genes that are coordinately regulated by controlling elements. Nor does Kohne teach the use of probes of sequence specific neither to genus nor species or other taxonomic grouping.

The *E. coli* chromosome is circular and contains seven operons for rRNA (FIG. 1). A typical rRNA (rrn) operon contains two promoters and genes for 16S, 23S, and 5S rRNA and a single 4S tRNA gene (FIG. 2). When analyzed, the 16S genes of the different *E. coli* rrn operons have been found to have regions where the sequences have been altered through mutations (Table 1). In some operons the mutations are the same in one particular region and in other operons they are different. Other organisms such as Shigella may either have a different number of operons, different types of operons, a different proportion of a particular mutation in one or more of its operons, one or more mutations in its operons distinct from *E. coli* or all of these possibilities.

FIG. 1 is an illustration of the ribosomal RNA operon on the *E. coli* chromosome. Each line marks the relative positions of one of the seven rrn operons found on the *E. coli* chromosome.

FIG. 2 is an illustration of a ribosomal RNA operon.

nucleic acid fragments are formed. A useful measure of the stability of a DNA duplex or an RNA-DNA hybrid is the melting temperature or $T_m$, which refers to the temperature at which the strands are half dissociated or denatured. Complexity refers to the total length of different sequences present in a sample of nucleic acid. Reassociation is the process of joining together by typical base pairing the two fully separated complementary sequences. Complementary refers to rules of base pairing enunciated by Erwin Chargaff whereby an adenine base pairs with its thymine complement and a guanine base pairs with its cytosine complement.

Hybridization reactions are usually done in a buffered, aqueous medium that may contain other additives. Additives may include detergent, salts, polymers, and blocking agents. The stringency of the hybridization medium may be controlled by temperature, salt concentration, probe concentration, probe length, time, and other factors. The rate

TABLE 1

Subsequence Variation in the Ribosomal RNA Operons of *E. coli*

| Operon or Strain | Nucleotide Position | Sequence Variant | SEQ ID NO |
|---|---|---|---|
| ECORRD | 71–100 | AACAGGAAGA AGCTTGCTCT TT     GCTGACGA | 5 |
| rrnG | 71–100 | --------AC --------G- --/C\-------- | 6 |
| rrnE | 71–100 | ---------- ------/T\- --  -------- | 7 |
| rrnC | 71–100 | --------AC ---------- --/C\------- | 8 |
| rrnB | 71–100 | ---------- ------/T\- --  -------- | 9 |
| ATCC 25922 | 71–100 | --------CG ------/G\- --  -------- | 10 |
| ATCC 11775T | 71–100 | ---------C ------/G\- --  -------- | 11 |

The number of possible potential combinations suggests that hybridization of rrn operon subunit probes specific for 16S does not detect subsequences specific to a taxonomic unit but instead detects a variable number of a targeted mutation within the operons, the number and variability of which may differ from one closely related organism to another. Thus, the rrn operon subsequences for 16S not only exhibit phylogenetic variability between organisms but variability even within a given genus and species of a single organism.

Sequencing of 16S genes in rrn operons does not necessarily clarify the variability seen. The entire process of preparing a plasmid vector containing ligated genetic material from rrn operon 16S genes in order to conduct the sequencing studies fails generally to select either for a specific operon or for a single bacterial cell containing a vector carrying a single rrn operon. DNA representing the rrn operon 16S subsequences, for example, prepared from Shigella is amplified in the polymerase chain reaction (PCR) using universal primers that are unlikely to discriminate between subsequences from one operon and another. Competent cells carrying the ligated vector are then selected for large-scale cloning. A colony of cells, rather than a single cell or cell clone, is chosen.

In all cases of selection for the sequencing process, heterogenous rrn operon material rather than homogenous rrn operon nucleic acid may be obtained. The resulting genetic sequences may either then represent a broad consensus sequence from all the possible rrn operon subsequences or a skewed sequence representing some but not all of the rrn operons and their different subsequences. This makes it very difficult to predict from the rrn sequences which probe subsequences are most likely to differentiate between one taxonomic group and another.

Hybridization refers to the process whereby sequence-specific, base-paired duplexes from any combination of of reassociation of two simple DNA strands with complementary sequences and no significant sequence repetition is easily described by practical kinetic equations such as (1) and (2) given below.

$$H=(1+kC_o t)^{-1} \qquad (1)$$

where H=fraction of DNA not bound to hydroxyapatite, k=observed rate constant, $C_o$=original concentration of nucleotides, and t=time in seconds. Hydroxyapatite is used to distinguish single-stranded DNA from double-stranded DNA.

$$S=(1+kC_o t)^{-0.44} \qquad (2)$$

where S=fraction of nucleotides remaining unpaired based on the use of nuclease S1 to differentiate single and double-stranded DNA.

The kinetics describing the rate of reassociation for complex genomes with sequence repetition is more difficult, particularly if bound to a filter or other surface such as an optic fiber. Although bacteria have relatively simple genomes compared to higher organisms, the repetition and multiplicity of the rrn operons in bacteria make their hybridization reactivity difficult to predict. For example, as stringency is increased, sequences that are not perfectly complementary should become less stable. The extent of hybridization of a probe to a given bacterial genome, therefore, might be expected to decrease with increasing temperature if there were some mismatching of bases or, at best, stay the same if there was perfect complementarity.

Stringency washes are usually performed at 3–5° C. below the $T_m$ of the perfectly matched probe when differentiation from mismatched sequences is required. The Wallace rule (R. B. Wallace and C. G. Miyada, *Methods in Enzymology* 152:438, 1990) can be used as follows to calculate the $T_m$ for a probe in order to set the temperature conditions necessary to avoid mismatched sequences:

$$T_m = (4 \times \text{number of } G+C \text{ bases}) + (2 \times \text{number of } A+T \text{ bases}) \quad (3)$$

However, when the $T_m$ is calculated in this matter for each of the probes of the present invention, it is found to be more than 5° below the actual $T_m$ as measured in 1 M NaCl. This discrepancy further complicates a determination of stringency for rrn operon analysis. The method of the present invention provides conditions for hybridization of the probes that exceeds the calculated $T_m$ and ensures that stringent conditions are being employed.

Previous studies have shown that a bell-shaped curve describes the relationship between the rate of hybridization and the temperature of incubation for formation of well-matched hybrids (Margaret L. M. Anderson and Bryan D. Young, Quantitative Filter Hybridization, in Roy J. Britten and Eric H. Davidson, *Nucleic Acid Hybridization*, Academic Press, 1985). The curves show a low relative rate of reassociation of perfectly matched sequences at either end (−50° C. below the $T_m$ and at the $T_m$) of the bell curve and a maximal rate of reassociation at −20° C. below the $T_m$. The rate of reassociation for mismatched sequences falls to zero at −20° C. below the $T_m$.

Such studies do not teach the hybridization reactivity seen when the probes of the present invention directed toward rrn operon 16S subsequences are hybridized at temperatures above their calculated $T_m$. The studies do not generally predict a loss of hybridization reactivity at temperature a few degrees below the measured $T_m$ followed by a reappearance of hybridization reactivity as the temperature approaches the measured $T_m$ of the probe. This phenomenon is seen, however, for some but not all of the probes used to test *E. coli* and the Shigella species reported herein. The reactivity of these particular probes with bacterial genomes have neither been previously disclosed or discussed.

The present invention also provides a method for organizing the complexity of probe reactivity with *E. coli* and Shigella organisms into a hierarchical flow diagram for identifying one or more of these closely related organisms when present in a sample.

In another aspect, the present invention contemplates a diagnostic kit for screening a test sample for the presence of Shigella species or *E. coli*. Such a kit would contain a nucleic acid probe having specificity for a species specific or genus specific nucleotide.

DETAILED DISCLOSURE OF THE INVENTION

Figure 1:
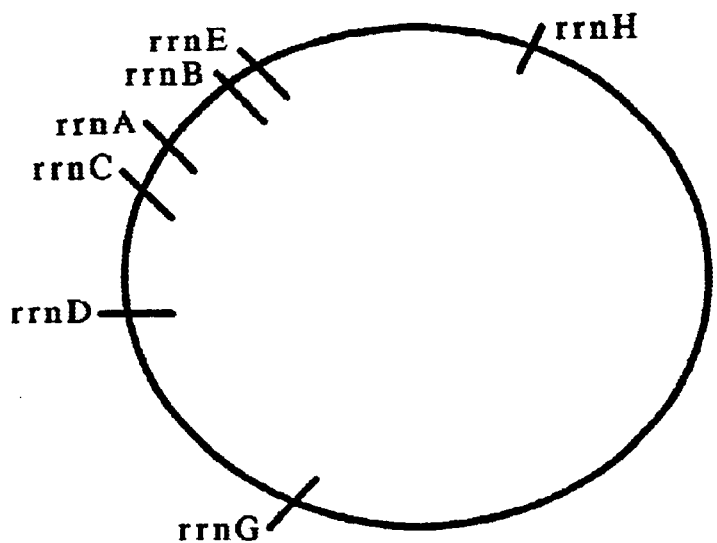
FIG. 1 is an illustration of the organization of ribosomal RNA operons on the *E. coli* Chromosome. Each line marks the relative position of one of the seven rrn operons found on the *E. coli* chromosome.
Figure 2:
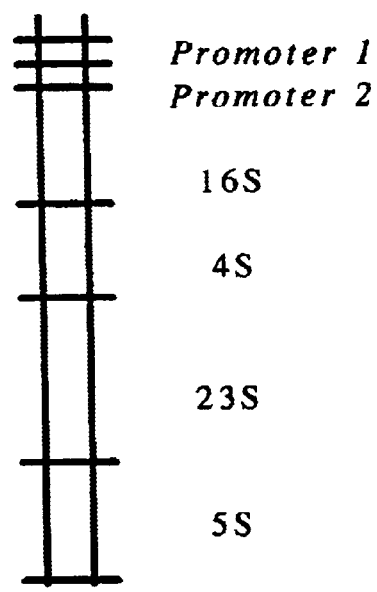
FIG. 2 is an illustration of the internal organization of a ribosomal RNA Operon.
Figure 3:
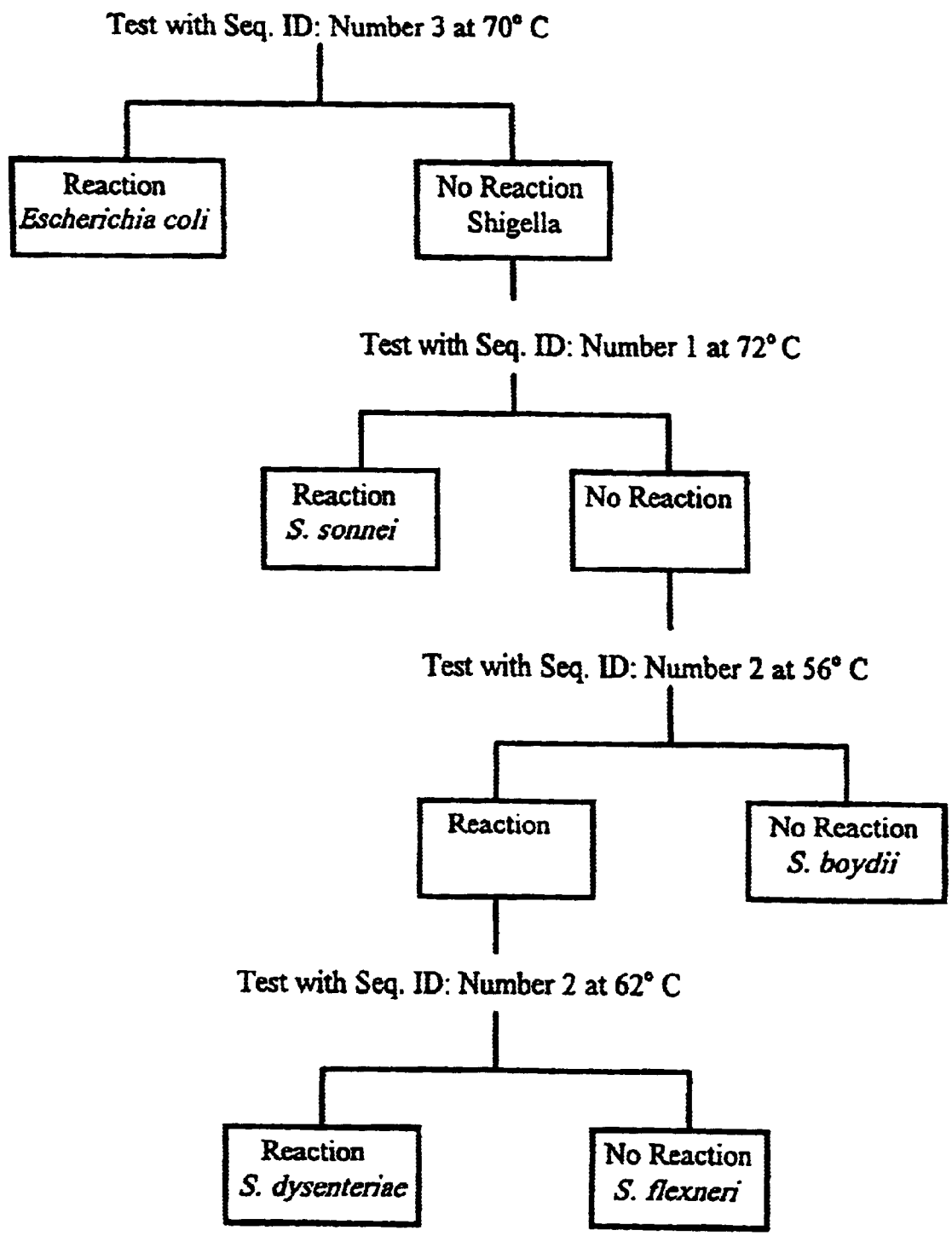
FIG. 3 is a flow diagram of a hybridization strategy to separate *E. coli* from Shigella and to separately identify Shigella species. The strategy shown in FIG. 3 has been used to first separately determine whether a sample is *E. coli* or Shigella and then, if Shigella, determine which of the four species it is.

The present invention provides a method and means for detecting, identifying, and quantifying Shigella in biological and other samples and more specifically for sensitively detecting and quantifying such organisms. For example, the 16S nucleotide subsequences of the rrn operons have been analyzed in order to develop probes for variable reactivity with the operons of different species of Shigella and *E. coli*.

*Some* 16S sequences are discussed in U.S. Provisional patent application Serial No. 60/038,117, filed Feb. 20, 1997, specifically incorporated herein by reference.

Hybridization is conducted by dot blot on nylon filters, but other methods such as solution hybridization and covalent attachment to a solid surface such as an optical fiber for sandwich hybridization are possible as are variations in the composition of the prehybridization, hybridization, and wash buffers and the methods for detecting when hybridization has occurred such as the use of chemiluminescence, bioluminescence, fluorophores, and others. The present embodiments can also be employed using a near-infrared optical fiber evanescent field-excited fluorosensor (Saeed Pilevar et al., Ser. No. 08/866,080, abandoned, filed May 30, 1997 specifically incorporated herein by reference).

In the preferred embodiment, a method for discriminating among members of a taxonomic group by hybridization analysis of operon subsequences has been determined. Either RNA or DNA from *E. coli* and Shigella can serve as the target for these probes. A sample is tested for rrn operon 16S subsequence reactivity by hybridization to each probe under various conditions to ensure increasing levels of stringency. The operon subsequence reactivity is tested by using each oligonucleotide probe under controlled stringency conditions at two or more wash temperatures relative to the probe's calculated or experimentally determined $T_m$. The hybridization reactions are then assayed to determine the relative level of reactivity of the combined operon 16S subsequences that may be present.

Four probes for distinguishing between the genera Escherichia and Shigella and their species are the subject of the present invention. The probes are identified as follows:

```
1. SEQ ID NO 1 has the sequence
   CAG CTT GCT CTT CGC TGA CG.

2. SEQ ID NO 2 has the sequence
   AAA GCA GCT TGC TCT TTG CT.

3. SEQ ID NO 3 has the sequence
   CGA CGC AAC GCG AAG AAC TT.

4. SEQ ID NO 4 has the sequence
   GAA GCT TGC TTC TTT GCT GAC.
```

Kits containing probe molecules capable of detecting the presence of species specific or genus specific nucleotides in the test sample are part of the invention. A test kit may include nucleic acid molecules having a nucleotide sequence of Seq. ID Nos 1–4.

The following Shigella species were obtained from the American Type Culture Collection for the study: *S. boydii* (8700), *S. dysenteriae* (13313), *S. flexneri* (29903), and *S. sonnei* (29930).

*Escherichia coli* O157:NM (G5066) was obtained from the Centers for Disease Control and Prevention.

EXAMPLE 1

Production of a Probe that will Hybridize and Distinguish *E. coli* and *S. sonnei* from other Species of Shigella A probe sequence (SEQ ID NO: 1) was identified for the 71–100 nucleotide position of the rrn operon 16S subsequence of *S. boydii*. This regional sequence has not been reported for any of the corresponding rrn operon 16S subsequences of *E. coli*, for the rrn operon subsequence of another strain of *S. boydii*, or for the corresponding rrn operon subsequences for other species of Shigella. Without hybridization analysis of the rrn operons in *E. coli* and Shigella, it would be difficult to predict the extent to which, if any, this probe would react with these organisms. The measured $T_m$ for the probe in 1 M NaCl is 72° C. whereas the calculated $T_m$ is 64° C.

Accordingly, DNA samples from each species of Shigella and from *E. coli* were prepared by standard phenol extraction (F. Ausebel et. al., Eds. *Current Protocols in Molecular Biology*, John Wiley & Sons, New York, 1989). DNA was denatured by heating on 0.2 N NaOH at 37° C. for 10 minutes. Blots were prepared by spotting solutions of each DNA preparation (40 μg/blot) on Nytran filters (Schleicher & Schuell). DNA was crosslinked to the filter in a Stratalinker (Strategene) by applying 120,000 mjoules of ultraviolet light to the surface. Filters were prehybridized with buffer consisting of 6×SSC, 3% blocking powder (Boehringer-Mannheim), and 0.5% Tween 20 heated to 60° C. For preparing the prehybridization solution, the components were added and the solution was then heated at 70° C. for 20 minutes before being cooled to room temperature. 5'-Labeled biotin probes were added directly to the prehybridization buffer, and samples were incubated for either 2 hours or overnight.

After hybridization was complete, filters were washed in 6×SSC twice for 5 minutes each time at room temperature and then once in 6×SSC for 10 minutes at the wash temperature indicated. Filters were next transferred to a detection blocking buffer that consisted of 6×SSC, 0.35% blocking powder, and 0.1% Tween 20. The filters were incubated in this buffer at room temperature for 20–30 minutes with gentle rocking.

A conjugate of streptavidin and horseradish peroxidase (KPL Labs) at a 1:500 dilution (0.1 mg/ml, 40 μl total) was added directly to the detection blocking buffer, and the filters were incubated at room temperature for an additional 20 minutes without shaking. Filters were than transferred to a clean container and washed 3 times with 1× membrane wash buffer (KPL Labs). Each wash was carried out at room temperature for 5 minutes with gentle shaking.

Just prior to use, equal volumes of the HRP detection reagents (KPL Labs) (luminol and $H_2O_2$) were mixed together, and then added to the filters in a clean container. After a 60-second incubation, the filters were wrapped in Saran Wrap, and exposed to Hyperfilm (Amersham) x-ray film. Exposures ranging from 10 minutes to overnight were made as needed.

TABLE 2

| | Seq ID Number 1 | | |
|---|---|---|---|
| Organism | 62° | 66° | 72° |
| Shigella boydii | + | + | – |
| Shigella dysenteriae | + | + | – |
| Shigella flexneri | + | + | – |
| Shigella sonnei | + | + | + |
| Escherichia coli | + | + | + |

The results suggest that *E. coli* and the four species of Shigella have operons capable of reacting with this probe under high stringency, but that only *S. sonnei* and *E. coli* operon subsequences remain reactive at the observed $T_m$. Although based on sequence differences seen for the *S. boydii* operon analysis, this probe is useful for the identification of *S. sonnei* and/or *E. coli* operon subsequences when used at 72° C. for DNA-DNA hybridization. The reactivity of this probe at 72° C. indicates that the probe is not specific for a particular taxonomic group since it recognizes both *S. sonnei* and *E. coli* operon subsequences but fails to recognize subsequences for other members of the genus to which *S. sonnei* belongs. Although derived from *S. boydii* sequences, the probe at 72° fails to recognize *S. boydii*.

EXAMPLE 2
Production of a Probe that will Hybridize and Distinguish Shigella sonnei and *E. coli* from other Species of Shigella or *S. dysenteriae* from *E. coli* and other Species of Shigella Probe SEQ. ID NO. 2 is based on a sequence determined from *S. dysenteriae*. This probe has a calculated $T_m$ of 58° C. and a measured $T_m$ in 1 M NaCl of 66° C.

TABLE 3

| | Seq. ID: Number 2 | | |
|---|---|---|---|
| | Wash Temperature (C.) | | |
| Organism | 56° | 66° | 62° |
| Shigella boydii | – | – | – |
| Shigella dysenteriae | + | – | + |
| Shigella flexneri | + | – | – |
| Shigella sonnei | + | + | – |
| Escherichia coli | + | + | – |

This probe also fails to distinguish rrn operon subsequences of either genus or species. At 56° C. it reacts with *E. coli* and *S. dysenteriae*, *S. flexneri*, and *S. sonnei* but not with *S. boydii*. At 66° C. it still reacts with two different species, *S. sonnei* and *E. coli*, but not with other Shigella species, thereby failing to distinguish a specific taxonomic group. Under the most stringent hybridization conditions, this probe fails to react with *S. dysenteriae*, the organism from which the probe sequence was derived.

EXAMPLE 3
Production of a Probe that will Hybridize and Distinguish *E. coli* from Shigella The probe based on SEQ. ID NO. 3 is derived from a *S. sonnei* sequence, with a calculated $T_m$ of 62° C. and a measured $T_m$ in 1 M NaCl of 70° C.

TABLE 4

| | Seq. ID: Number 3 | |
|---|---|---|
| | Wash Temperature (C.) | |
| Organism | 66° | 70° |
| Shigella boydii | – | – |
| Shigella dysenteriae | + | – |
| Shigella flexneri | + | – |
| Shigella sonnei | + | – |
| Escherichia coli | + | + |

This probe should show homology with the *S. sonnei* operon 16S subsequence but not with any of the corresponding *E. coli* operon 16S subsequences. Nevertheless, the probe crosses genus and species categories at 66° and hybridizes at 70° with *E coli* operon 16S subsequences but not with *S. sonnei* operon 16S subsequences from which the probe was derived.

EXAMPLE 4
Production of a Probe that will Hybridize and Distinguish *E. coli* from Shigella The probe labeled SEQ. ID NO. 4 is specific to some but not all rrn operon 16S subsequences ascribed to this region of *E. coli*. However, since it is unlikely that all rrn operon 16S subsequences for Shigella in this region have been sequenced for the reasons noted previously, it cannot be stated with certainty that this subsequence is specific only to *E. coli*. The $T_m$ for this probe when calculated is 62° C. and when measured in 1 M NaCl is 69° C. This probe reacts solely with *E. coli* at 69° C.

Table 5 shows the specificity of the probes determined by testing each one at one or more wash temperatures with DNA prepared from each of six other species of enteric bacteria closely related to *E. coli* and Shigella. Samples of each bacterium were obtained from the American Type Culture Collection. The following strains were used: *Citrobacter freundii* (8090), *Klebsiella pneumoniae* (13883), *Proteus vulgaris* (13315), *Salmonella choleraesuis* (14028), *Serratia marescens* (13880), and *Yersinia enterocolitica* (9610). The results indicate that the probes do not cross-react with operon 16S subsequence variants found in any of the other organisms tested.

TABLE 5

Specificity of Operon-Based 16S Subsequence Probes

| Probe | Temperature | Organism | Reactivity |
|---|---|---|---|
| SEQ ID NO 1 | 72° | *Citrobacter freundii* | – |
| | | *Klebsiella pneumoniae* | – |
| | | *Proteus vulgaris* | – |
| | | *Salmonella choleraesuis* | – |
| | | *Serratia marescens* | – |
| | | *Yersinia enterocolitica* | – |
| SEQ ID NO 2 | 56° | *Citrobacter freundii* | – |
| | | *Klebsiella pneumoniae* | – |
| | | *Proteus vulgaris* | – |
| | | *Salmonella choleraesuis* | – |
| | | *Serratia marescens* | – |
| | | *Yersinia enterocolitica* | – |

TABLE 5-continued

Specificity of Operon-Based 16S Subsequence Probes

| Probe | Temperature | Organism | Reactivity |
|---|---|---|---|
| SEQ ID NO 2 | 62° | *Citrobacter freundii* | – |
| | | *Klebsiella pneumoniae* | – |
| | | *Proteus vulgaris* | – |
| | | *Salmonella choleraesuis* | – |
| | | *Serratia marescens* | – |
| | | *Yersinia enterocolitica* | – |
| SEQ ID NO 3 | 66° | *Citrobacter freundii* | – |
| | | *Klebsiella pneumoniae* | – |
| | | *Proteus vulgaris* | – |
| | | *Salmonella choleraesuis* | – |
| | | *Serratia marescens* | – |
| | | *Yersinia enterocolitica* | – |
| SEQ ID NO 4 | 69° | *Citrobacter freundii* | – |
| | | *Klebsiella pneumoniae* | – |
| | | *Proteus vulgaris* | – |
| | | *Salmonella choleraesuis* | – |
| | | *Serratia marescens* | – |
| | | *Yersinia enterocoltica* | – |

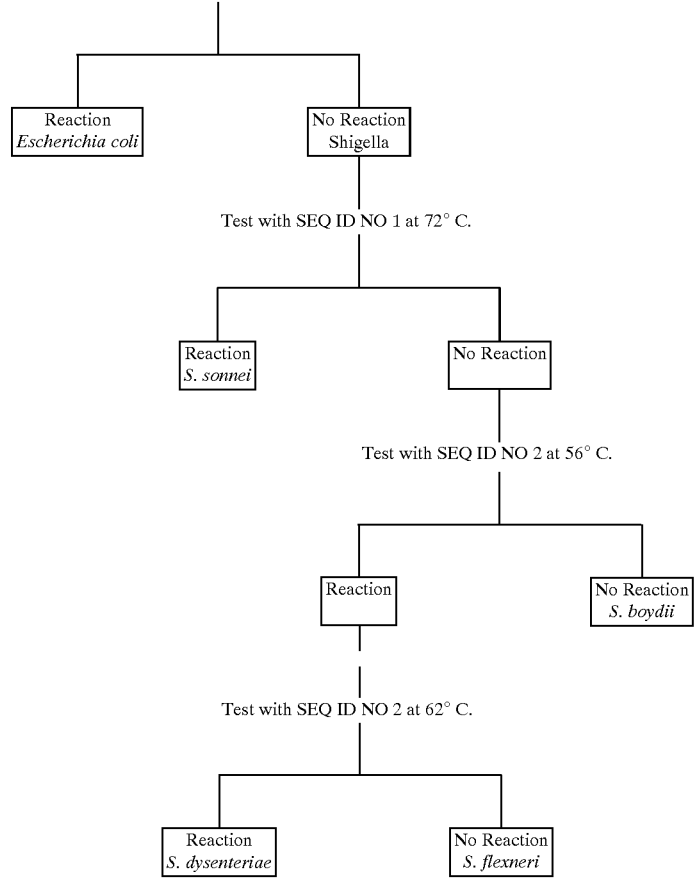

What is claimed is:

1. A method for discriminating between species of Shigella and *E. coli* or for discriminating among species of Shigella and *E. coli* in a sample containing organisms of one or more taxonomic groups comprising:
   a. selecting an oligonucleotide having a sequence from a DNA or RNA operon, wherein the sequence differs by one or more bases from at least one of the operons from the two or more species being discriminated, and wherein the oligonucleotide discriminates between species after hybridization by the use of two or more wash temperatures, at least one of which is above the oligonucleotide's calculated $T_m$;
   b. hybridizing the oligonucleotide to nucleic acid from the sample;
   c. exposing the hybridized oligonucleotide to two or more wash temperatures, at least one of which is above the oligonucleotide's calculated $T_m$; and
   d. determining the presence or absence of hybridized nucleic acid.

2. The method of claim 1, wherein an oligonucleotide comprising SEQ ID NO: 1 is used to discriminate between or among Shigella and Escherichia.

3. The method of claim 1, wherein an oligonucleotide comprising SEQ ID NO: 2 is used to discriminate between or among Shigella and Escherichia.

4. The method of claim 1, wherein an oligonucleotide comprising SEQ ID NO: 3 is used to discriminate between or among Shigella and Escherichia.

5. The method of claim 1, wherein an oligonucleotide comprising SEQ ID NO: 4 is used to discriminate between or among Shigella and Eacherichia.

6. The method of claim 1, wherein an oligonucleotide of RNA is used, wherein the oligonucleotide sequence comprises a sequence selected from the group consisting of SEQ. ID. Nos.: 1, 2, 3 and 4, and wherein U substitutes for T.

7. A nucleic acid probe comprising the sequence of SEQ ID NO: 2 or 3, which distinguishes between species of Shigella in a hybridization assay, or distinguishes between Shigella and *E. coli* in a hybridization assay.

8. A method for discriminating between species of Shigella and *E. coli* or for discriminating among species of Shigella and *E. coli* in a sample containing organisms of one or more taxonomic groups comprising:
   a. selecting an oligonucleotide having a sequence from a DNA or RNA operon, wherein the sequence differs by one or more bases from at least one of the operons from the two or more species being discriminated, and wherein the oligonucleotide discriminates between species after hybridization by the use of two or more wash temperatures at or above the oligonucleotide's calculated $T_m$ or at the experimentally determined $T_m$;
   b. hybridizing the oligonucleotide to nucleic acid from the sample;
   c. exposing the hybridized oligonucleotide to two or more wash temperatures at or above the oligonucleotide's calculated $T_m$ or at the experimentally determined $T_m$; and
   d. determining the presence or absence of hybridizing nucleic acid, wherein said oligonucleotide consists of the sequence of SEQ ID NO: 4 or wherein said oligonucleotide comprises a sequence selected from the group consisting of SEQ ID NO: 1, SEQ ID NO: 2 and SEQ ID NO: 3.

9. The method of claim 8, wherein an oligonucleotide consisting of SEQ ID NO: 1 is used to discriminate between or among Shigella and Escherichia.

10. The method of claim 8, wherein an oligonucleotide consisting of SEQ ID NO: 4 is used to discriminate between or among Shigella and Escherichia.

11. The method of claims 8, wherein an oligonucleotide of RNA is used, wherein the oligonucleotide sequence consists of a sequence selected from the group consisting of SEQ ID NOs: 1, 2, 3 or 4, and wherein U substitutes for T.

12. The method of claim 1, wherein an oligonucleotide consisting of SEQ ID NO: 1 is used to discriminate between or among Shigella and Escherichia.

13. The method of claim 1, wherein an oligonucleotide consisting of SEQ ID NO: 2 is used to discriminate between or among Shigella and Escherichia.

14. The method of claim 1, wherein an oligonucleotide consisting of SEQ ID NO: 3 is used to discriminate between or among Shigella and Escherichia.

15. The method of claim 1, wherein an oligonucleotide consisting of SEQ ID NO: 4 is used to discriminate between or among Shigella and Escherichia.

16. A nucleic acid probe which consists of the sequence of SEQ ID NO: 1 which distinguishes between species of Shigella in a hybridization assay, or distinguishes between Shigella and *E. coli* in a hybridization assay.

17. The nucleic acid probe of claim 7, which comprises the sequence of SEQ ID NO: 2.

18. The nucleic acid probe of claim 7, which consists of the sequence of SEQ ID NO: 2.

19. The nucleic acid probe of claim 7, which comprises the sequence of SEQ ID NO: 3.

20. The nucleic acid probe of claim 7, which consists of the sequence of SEQ ID NO: 3.

21. A kit, comprising 3 probes, which are a probe which comprises the sequence of SEQ ID NO: 1, a probe which comprises the sequence of SEQ ID NO: 2, and a probe which comprises the sequence of SEQ ID NO: 3.

22. A kit, comprising 3 probes, which are a probe which consists of the sequence of SEQ ID NO: 1, a probe which consists of the sequence of SEQ ID NO: 2, and a probe which consists of the sequence of SEQ ID NO: 3.

23. The kit of claim 21, further comprising a probe which comprises the sequence of SEQ ID NO: 4.

24. The kit of claim 22, further comprising a probe which comprises the sequence of SEQ ID NO: 4.

25. A method as in claim 1 wherein the oligonucleotide is hybridized to nucleic acid within the sample and the sample is separated into at least two portions and each portion contains nucleic acid from the hybridized oligonucleotide and is exposed to a different wash temperature, at least one of which is above the oligonucleotide's calculated $T_m$.

26. A method as in claim 8 wherein the oligonucleotide is hybridized to nucleic acid within the sample and the sample is separated into at least two portions and each portion contains nucleic acid from the hybridized oligonucleotide and is exposed to a different wash temperature, at least one of which is above the oligonucleotide's calculated $T_m$.

27. A method of using a nucleic acid probe of claim 7 to discriminate between Shigella and *E. coli* or among species of Shigella and *E. coli* in a sample which comprises the step of hybridizing said nucleic acid probe to nucleic acid in the sample.

28. A method of using a kit of claim 22 to discriminate between Shigella and *E. coli* or among species of Shigella and *E. coli* in a sample which comprises the step of hybridizing the probes of said kit to nucleic acid in the sample.

29. The method of claim 27, wherein a nucleic acid probe consisting of SEQ ID NO: 2 is used to discriminate between or among Shigella and Escherichia.

30. The method of claim 27, wherein a nucleic acid probe consisting of SEQ ID NO: 3 is used to discriminate between or among Shigella and Escherichia.

* * * * *

UNITED STATES PATENT AND TRADEMARK OFFICE
CERTIFICATE OF CORRECTION

PATENT NO. : 6,727,061 B2 Page 1 of 1
DATED : April 27, 2004
INVENTOR(S) : Frank H. Portugal It is certified that error appears in the above-identified patent and that said Letters Patent is hereby corrected as shown below:

Title page,
Item [54], Title, should read as -- METHODS FOR IDENTIFYING SPECIES OF SHIGELLA AND *E . COLI* USING OPERON SEQUENCE ANALYSIS --.
Item [73], Assignee, should read as -- Cabtech, Inc. --

Signed and Sealed this

Sixteenth Day of November, 2004

JON W. DUDAS
*Director of the United States Patent and Trademark Office*